United States Patent
Lin

(10) Patent No.: US 9,539,184 B2
(45) Date of Patent: Jan. 10, 2017

(54) COLLOIDAL FACIAL MASK WITH PARTIAL CARRIER AND METHOD FOR MANUFACTURING THE SAME

(71) Applicant: Yu-Yueh Lin, Taipei (TW)

(72) Inventor: Yu-Yueh Lin, Taipei (TW)

( * ) Notice: Subject to any disclaimer, the term of this patent is extended or adjusted under 35 U.S.C. 154(b) by 0 days.

(21) Appl. No.: 14/656,325

(22) Filed: Mar. 12, 2015

(65) Prior Publication Data

US 2016/0120766 A1    May 5, 2016

(30) Foreign Application Priority Data

Oct. 29, 2014  (TW) .............................. 103137499 A

(51) Int. Cl.

| | |
|---|---|
| *A61K 8/02* | (2006.01) |
| *A61K 8/73* | (2006.01) |
| *A45D 44/00* | (2006.01) |
| *A61Q 19/08* | (2006.01) |
| *A61Q 19/02* | (2006.01) |

(52) U.S. Cl.
CPC ........... *A61K 8/0212* (2013.01); *A45D 44/002* (2013.01); *A61K 8/731* (2013.01); *A61K 8/733* (2013.01); *A61Q 19/02* (2013.01); *A61Q 19/08* (2013.01)

(58) Field of Classification Search
CPC ....... A61K 8/0212; A61Q 19/08; A61Q 19/02
See application file for complete search history.

(56) References Cited

U.S. PATENT DOCUMENTS

| | | | |
|---|---|---|---|
| 5,144,016 | A | 9/1992 | Skjak-Braek et al. |
| 5,230,853 | A | 7/1993 | Colegrove et al. |
| 5,622,666 | A | 4/1997 | Struszczyk et al. |
| 5,660,857 | A | 8/1997 | Haynes et al. |
| 5,675,957 | A | 10/1997 | Kim |
| 6,080,420 | A | 6/2000 | Qin et al. |
| 6,201,164 | B1 | 3/2001 | Wulff et al. |
| 6,203,845 | B1 | 3/2001 | Qin et al. |
| 6,258,995 | B1 | 7/2001 | Gilding et al. |
| 6,326,524 | B1 | 12/2001 | Fattman et al. |
| 6,372,248 | B1 | 4/2002 | Qin et al. |
| 2005/0287193 | A1 | 12/2005 | Lee |

(Continued)

FOREIGN PATENT DOCUMENTS

| | | | | |
|---|---|---|---|---|
| CN | 202459409 U | * | 3/2012 | ............... A61K 8/02 |
| CN | 203885878 U | * | 10/2014 | ............... A61K 8/73 |

(Continued)

*Primary Examiner* — Aradhana Sasan
(74) *Attorney, Agent, or Firm* — Muncy, Geissler, Olds & Lowe, P.C.

(57) ABSTRACT

A colloidal facial mask with a partial carrier is revealed. The colloidal facial mask includes a colloidal layer and a carrier layer. The colloidal layer is made from colloidal film materials with high water absorption and having a first surface attached to user's face and a second surface opposite to the first surface. The carrier layer is attached and connected to at least one partial area of the second surface of the colloidal layer so as to increase mechanical strength thereof. The partial area can be an eye part, a nose part, or a mouth part. There is a partial area of the second surface of the colloidal layer not covered by the carrier layer so that the cost of the carrier layer is reduced. Moreover, the carrier layer can be preset with patterns or markers according to user's needs.

15 Claims, 9 Drawing Sheets

(56) References Cited

U.S. PATENT DOCUMENTS

2006/0212996 A1* 9/2006 McGrath ............ A41D 13/1161
                                                          2/207
2010/0227164 A1 9/2010 Hihnala et al.

FOREIGN PATENT DOCUMENTS

| EP | 2 111 926 A1 | 10/2009 | |
|---|---|---|---|
| JP | 2010-189386 A | 9/2010 | |
| JP | 2014-133715 A * | 7/2014 | .............. A61K 8/73 |
| WO | WO96/10106 A1 | 4/1996 | |
| WO | WO97/03710 A1 | 2/1997 | |
| WO | WO97/39781 A1 | 10/1997 | |
| WO | WO98/02196 A1 | 1/1998 | |
| WO | WO99/20378 A1 | 4/1999 | |
| WO | WO03/092754 A1 | 11/2003 | |
| WO | WO2008/072817 A1 | 6/2008 | |

* cited by examiner

COLLOIDAL FACIAL MASK WITH PARTIAL CARRIER AND METHOD FOR MANUFACTURING THE SAME

BACKGROUND OF THE INVENTION

The present invention relates to a colloidal facial mask with a partial carrier and a method for manufacturing the same, especially to a colloidal facial mask having a colloidal layer and a carrier layer attached to at least one partial area of one surface of the colloidal layer while the rest area of the colloidal is not covered by the carrier layer.

Generally, the colloidal facial mask is divided into two types while in use-without carriers or with carriers. The colloidal facial mask without carriers includes only a colloidal layer with a certain thickness such as alginate layer, but not limited, while the colloidal facial mask with carriers consists of a colloidal layer with a certain thickness and a carrier layer made from non-woven fabric (not limited) connected to each other. The carrier layer is connected to and integrated with the colloidal layer so that the two layers are unable or difficult to be separated. In the present invention, the colloidal facial mask is with carriers.

A conventional colloidal facial mask is formed by a colloidal layer and a carrier layer. The colloidal layer is made from colloidal film materials with high water absorption such as alginate, polymer gel, bio-cellulose, etc. so as to absorb solutions such as whitening agents or anti-wrinkle agent for cosmetic use. The carrier layer can be made from knitted fabric such as lace fabric, woven fabric, Jacquard fabric, etc or non-woven fabric but not limited. The carrier layer is attached and connected to whole surface of the colloidal layer (the surface here is defined as a rear surface). While in use, the user extends the colloidal facial mask and set a front surface of the colloidal layer (opposite to the rear surface with the carrier layer) on the face. Thus the solutions for cosmetic use container in the colloidal layer are contacted with and acted on the facial skin. Moreover, the shape of the conventional colloidal facial mask is not limited. It can be a half-face type, or full-face type. The full-face type covers the whole face while the half-face type covers a part of the face such as an upper face (including an eye part or a nose part) or a lower face (including a mouth part).

The colloidal facial masks are quite popular on the market so that both manufacturers and users (consumers) are concerned about development and improvement of the related techniques in following respects. (1) effect- how to make facial masks for cosmetic use have better effect? (2) convenience in use: how to allow users use facial masks more conveniently? (3) safety in use: how to improve safety and quality of facial masks? For example, whether the microorganism growth is effectively controlled or not. Is the facial mask preservative free? Do the materials for the facial mask match requirements for environmental protection? (4) appearance: how to provide users more options and let them have the desire of buying? (5) brand recognition: how to increase brand recognition and brand identity of users? (6) cost and price: how to mass-produce facial masks and increase their economic benefits. According to the different aspects mentioned above, the conventional colloidal facial mask in which the carrier layer is directly attached to the whole rear surface of the colloidal surface has following problems and shortcomings.

(1) The colloidal facial mask is attached to the face of the user but an eye part, a nose part, and a mouth part of the user are unable to be covered. Thus the colloidal facial mask is mounted with through holes corresponding to the eye part, the nose part, and the mouth part so that the eye, the nose part, and the mouth part are exposed. However, the through holes become fragile parts on the structure of the colloidal facial mask. Thus these parts are easy to be cracked or get broken when the user extends and puts the colloidal facial mask on the face.

(2) The carrier layer in the conventional colloidal facial mask is attached to the rear surface of the colloidal layer smoothly and used for reinforcing mechanical strength of the colloidal layer. When the carrier layer is made from materials with a certain thickness such as non-woven fabric, the colloidal facial mask is unable to be attached to projecting parts such as the eye part, the nose part, and the mouth part smoothly and completely. Thus the colloidal facial mask is easy to be released from the user's face in use. When the carrier layer is made from thin and light materials such as knitted fabric such as lace fabric, woven fabric, Jacquard fabric etc, the problem of insufficient attachment can be solved. However, the materials and manufacturing cost of the knitted fabric are higher. And the knitted fabric is only used as the carrier layer without additional functions and is discarded along with the colloidal facial mask after use. This causes a kind of waste and has negative effects on the market competitiveness of the colloidal facial mask.

(3) The conventional techniques used fro manufacturing the colloidal facial mask includes casting and continuous formation. Casting is a process by which materials for the colloidal layer and carrier layer are respectively poured into a mold, which contains at least one hollow cavity of the desired shape of the facial mask. Then a colloidal facial mask is solidified and molded. Although this method saves more materials for different layers, the method is not suitable for mass-production, especially for colloidal facial masks made from alginate. The continuous formation includes following steps. First a continuous long-strip base material having a colloidal layer and a carrier layer is produced. For example, the colloidal layer and the carrier layer are attached and connected on a conveyor. Then get a colloidal facial mask by cutting the continuous long-strip base material. This process uses more materials for the colloidal layer and the carrier layer. Yet this process is suitable for mass-production, especially for colloidal facial masks made from alginate. Therefore how to avoid the waste of the materials for the colloidal layer and the carrier layer (especially the carrier layer made from knitted fabric) becomes an important issue when manufactures intend to use the continuous formation for mass production.

(4) As to the colloidal facial masks available on the market now, the words or patterns related to manufacturers, brand logos, place of manufacturing, compositions, etc. are all labeled on the packing boxes (bags). After the colloidal facial mask being taken out or the user/consumer puts the facial mask on the face, the user/consumer is difficult to differentiate colloidal facial masks of different brands because the shapes or appearances of the colloidal facial masks of different brands are nearly the same. This has negative effects on marketing and management of the manufactures' brands, as well as the users' selection and brand identity. Moreover, this may result in unnecessary disputes in the future. For example, the user/consumer buys two brands of colloidal facial masks with different cosmetic effects (or different prices). After use, the user finds that one of the two masks is unable to achieve the expected cosmetic effect (as shown in the advertisement). Now the user is unable to find out the source of the colloidal facial masks after use if the shapes or appearances of the colloidal facial masks are having no features or special designs and difficult to be differentiated. Once the user/consumer intends to find out who should be accountable for the failure or request for the services, he/she is easy to have conflicts with the sellers. Thus bad money drives out good and the market share of good products is affected.

Refer to U.S. Pat. No. 6,080,420, U.S. Pat. No. 6,258,995, U.S. Pat. No. 6,203,845, U.S. Pat. No. 6,201,164, U.S. Pat. No. 6,372,248, U.S. Pat. No. 6,326,524, U.S. Pat. No. 5,144,016, U.S. Pat. No. 5,230,853, U.S. Pat. No. 5,622,666, U.S. Pat. No. 5,660,857, U.S. Pat. No. 5,675,957, U.S. Pat. No. 5,144,016, US2005/0287193, US2010/0227164; PCT/GB 9502284(WO96/10106), PCT/GB 9601719(WO97/03710), PCT/GB 9701098(WO97/39781), PCT/DK 9700292(WO98/02196), WO2008/072817, WO03092754, EP2111926A1(WO2008/0090892, PCT/JP2008/050822); JP2010-189386, WO99/20378A1, these are all prior arts related to facial masks. However, most of these prior arts provide no technical solutions for problems and shortcomings mentioned above.

Furthermore, the structural design of the colloidal facial mask that solves the problems mentioned above may cause certain problems during manufacturing processes of the colloidal facial masks. For example, an apparatus and a method for manufacturing facial masks revealed in EP2111926A1 are quite complicated. Moreover, the films are not continuously manufactured during the processes. Thus the facial masks are difficult to be mass-produced.

There is room for improvement and a need to provide a new design of a facial mask and a method for manufacturing the same that overcome the shortcomings and solve the problems mentioned above.

SUMMARY OF THE INVENTION

Therefore it is a primary object of the present invention to provide a colloidal facial mask with a partial carrier. The colloidal facial mask is formed by a colloidal layer and a carrier layer. The colloidal layer is made from colloidal film materials with high water absorption such as alginate, polymer gel, bio-cellulose, etc. so as to absorb solutions such as whitening agents or anti-wrinkle agents for cosmetic use. The shape of the colloidal layer can be a half-face, or full-face. The colloidal layer includes a first surface and a second surface opposite to the first surface. The first surface is attached to user's face so that the solutions are in contact with the skin of the face. The carrier layer is attached and connected to at least one partial area of the second surface of the colloidal layer. The partial area can be an eye part, a nose part, or a mouth part that is easily cracked so as to increase the mechanical strength of these parts. The rest part of the second surface of the colloidal layer is not covered by the carrier layer. Thereby the cost of the carrier layer is reduced. The colloidal facial mask has better effects in use and higher value.

It is another object of the present invention to provide a colloidal facial mask with a partial carrier thereof. The carrier layer is made from knitted fabric such as lace fabric, woven fabric, Jacquard fabric so as to form various knitted patterns, hollow-out patterns or markers for improving decorative effect and brand recognition of the colloidal facial mask.

It is a further object of the present invention to provide a colloidal facial mask with a partial carrier thereof. The carrier layer is made from non-woven fabric, being attached and connected to the colloidal layer during manufacturing processes, the carrier layer is preset with a plurality of insertion holes, hollow-out patterns or markers before being attached and connected to the colloidal layer so as to improve decorative effect of the appearance and the brand recognition. In the conventional full-face facial masks with non-woven carrier, the insertions holes are mounted after the non-woven fabric being attached and connected to the colloidal film. Thus the facial mask is easy to get damaged. The present invention can overcome this shortcoming.

It is a further object of the present invention to provide a method for manufacturing a colloidal facial mask with a partial carrier having a plurality of steps. Step 1: provide a continuous base material for colloidal facial masks on a conveying platform for cutting and the base material for colloidal facial masks is moved along a conveying direction of the conveying platform. The continuous base material for colloidal facial masks includes a continuous colloidal layer and at least one continuous carrier layer. The continuous colloidal layer consists of a first surface and a second surface opposite to the first surface. The continuous carrier layer is horizontally attached to, connected to and covered at least a partial area of the second surface of the continuous colloidal layer. Step 2: cutting the continuous base material for colloidal facial masks on the conveying platform to get a facial mask array including a plurality of facial masks arranged at a certain pattern. In each colloidal mask of the facial mask array, the carrier layer is located on at least one partial area of the second surface of the colloidal layer corresponding to the eye part, the nose part, and the mouth part of the facial mask, or two of their combinations. Step 3: take out each colloidal facial mask of the facial mask array to complete continuous manufacturing processes of the colloidal facial mask.

The carrier layer is horizontally attached and connected to the eye part of the colloidal layer, perpendicular to a central line of the facial mask.

The carrier layer can also be attached and connected to the eye part of the colloidal layer horizontally, perpendicular to the central line of the facial mask. The carrier layer is extended over the area above the eye part, covered over the upper half part of the colloidal layer.

The carrier layer is vertically attached and connected to the central part of the colloidal layer, along the central line of the facial mask. Thus the carrier layer covers the central part of the colloidal layer. The central part is defined as the area bilaterally symmetrical along the central line of the facial mask, extended from forehead downward to the lower jaw of the facial mask and including the eye part, the nose part, and the mouth part.

The conveying platform for cutting operation is a circulating conveying platform moving along the conveying direction, connected to and located after an apparatus for continuously manufacturing films. Thus the continuous base material for colloidal facial masks prepared by the apparatus for continuously manufacturing films is transported to the conveying platform and moved along the conveying direction to be cut during the movement.

DETAILED DESCRIPTION OF THE PREFERRED EMBODIMENTS

Figure 2:
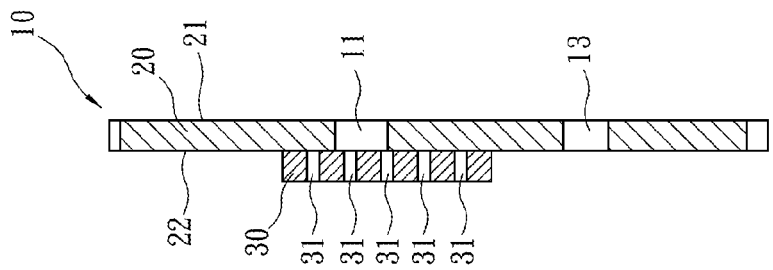
FIG. 2 is a schematic drawing showing an enlarged lateral cross section view of the embodiment in FIG. 1 according to the present invention.
Figure 1:
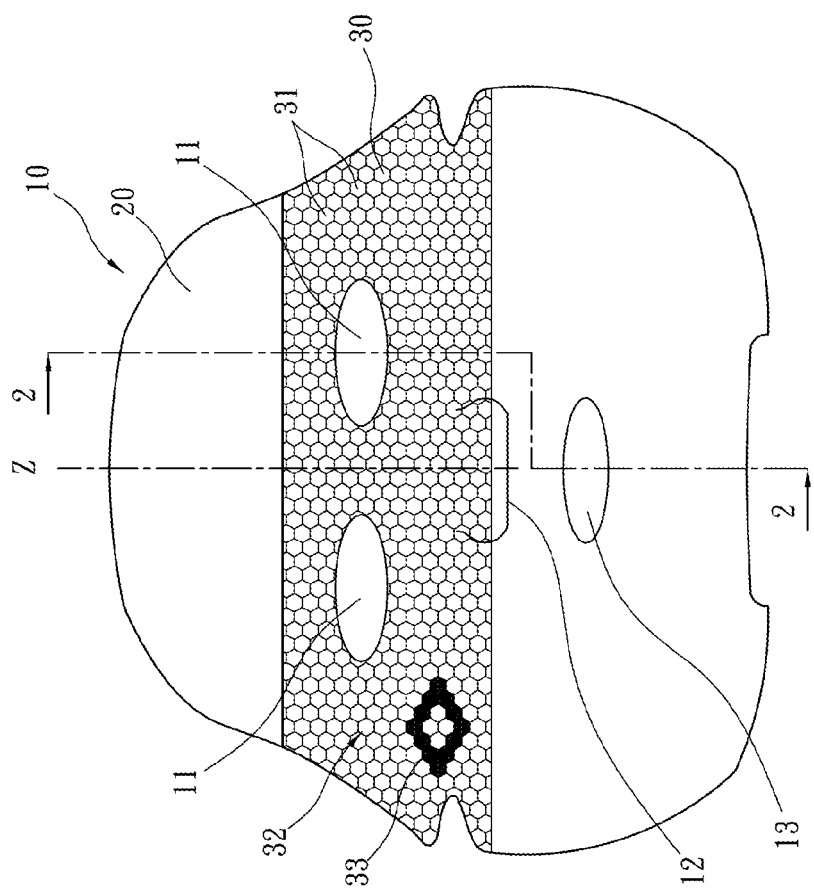
FIG. 1 is a schematic drawing showing a front view of an embodiment of the present invention.

Refer to FIG. 1 and FIG. 2, a colloidal facial mask 10 with partial carrier of the present invention includes a colloidal layer 20 and a carrier layer 30. The colloidal layer 20 is made from colloidal film materials with high water absorption such as alginate, polymer gel, bio-cellulose, etc. Due to high water absorption, the colloidal layer 20 contains solutions for cosmetic use such as whitening agents, anti-wrinkle agents, essence/serum, etc. The shape of the colloidal layer 20 can be a half-face, full-face or others according to users' needs. In FIG. 1, the colloidal layer 20 is a full-face mask. The colloidal layer 20 is formed by a first surface 21 and a second surface 22 opposite to the first surface 21. The first surface 21 is attached to the user's face (not shown in figure) so that the solutions for cosmetic use in the colloidal layer 20 work on facial skin.

In an embodiment of the colloidal facial mask 10, the carrier layer 30 is attached and connected to at least one partial area of the second surface 22 of the colloidal layer 20. The partial area includes an eye part 11, a nose part 12, a mouth part 3 and two of their combinations. In the embodiment shown in FIG. 1, the carrier layer 30 is horizontally attached to the eye part 11 of the colloidal layer 20, perpendicular to a central line Z of the facial mask 10. As shown in FIG. 1, the carrier layer 30 looks like a general eye cover. The eye part 11, the nose part 12, and the mouth part 13 of the facial mask 10 is fragile and easily cracked. When the carrier layer 30 is covered and attached to these parts of the colloidal layer 20, the mechanical strength of the colloidal facial mask 10 (or the colloidal layer 20) at these parts is increased. Moreover, the colloidal facial mask 10 is more convenient to use and the material cost of the carrier layer 30 is down.

In an embodiment of the colloidal facial mask 10, the carrier layer 30 is made from knitted fabric such as lace fabric, woven fabric, Jacquard fabric, etc. According to the properties the knitted fabric has, there are a plurality of tiny insertion holes arranged uniformly or non-uniformly at the carrier layer 30, as shown in FIG. 1 and FIG. 2. The size of the insertion hole 31 in FIG. 2 is an enlarged view, not in the real scale. These tiny insertion holes 31 will not affect water absorption and density of the colloidal layer 20.

In an embodiment of the colloidal facial mask 10, the carrier layer 30 can be preset to form various knitted patterns 32 with different shapes or at least one marker 33. The knitted patterns 32 can be uniform patterns (as one uniform pattern shown in FIG. 1), or non-uniform pattern (not shown in figure) while the marker 33 can be a trademark or a specific logo of a brand formed by knitted patterns hollow-out patterns. The marker 33 is located in the knitted pattern 32 obviously according to users' requirements. As shown in FIG. 1, the marker 33 is formed by a specific pattern. Moreover, compared with conventional facial, the colloidal facial mask 10 is more decorative and with higher brand recognition due to the masks he marker 30 having the knitted pattern 32 and or the marker 33 and attached and connected to at least one partial area of the second surface 22 of the colloidal layer 20.

In an embodiment of the colloidal facial mask 10, the carrier layer 30 is made from non-woven fabric. Refer to FIG. 2, before the carrier layer 30 (non-woven fabric) being attached and connected to the colloidal layer 20 during manufacturing processes, the carrier layer 30 (non-woven fabric) is preset with a plurality of insertion holes 31. There is no restriction on the number, the size and the shape of the insertion holes 31. As shown in FIG. 1, a plurality of hollow-out patterns 32 with different designs or at least one marker 33 is formed by the arrangement of the insertion holes 31 so as to improve the appearance and the brand recognition of the colloidal facial mask 10. Moreover, the conventional full-face facial masks with non-woven carriers are mounted with the insertion holes after the non-woven fabric being attached to the colloidal layer 20. The insertion holes may affect or damage the facial mask (colloidal layer 20). The present invention can avoid this shortcoming.

Figure 4:
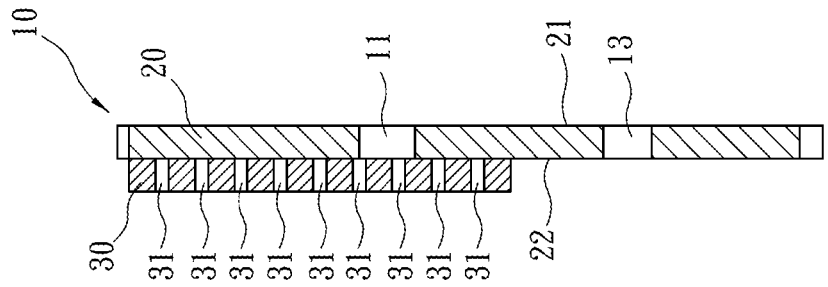
FIG. 4 is a schematic drawing showing an enlarged lateral cross section view of the embodiment in FIG. 3 according to the present invention.
Figure 3:
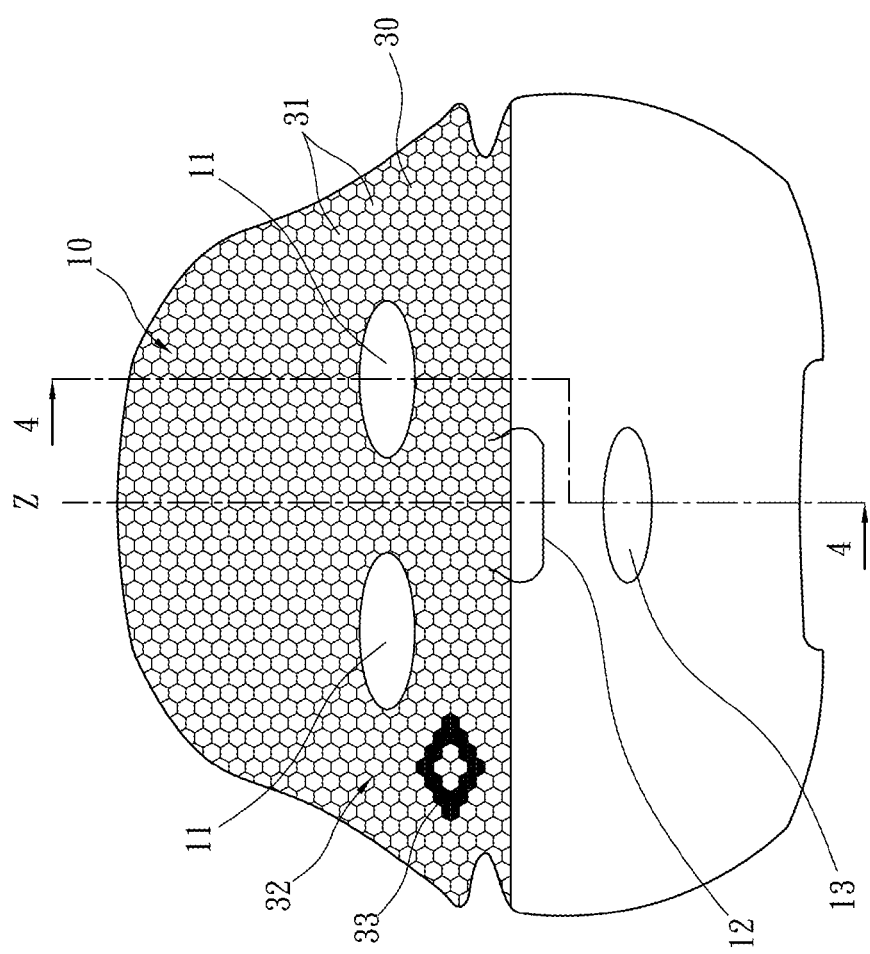
FIG. 3 is a schematic drawing showing a front view of another embodiment of the present invention.

Refer to FIG. 3 and FIG. 4, another embodiment is revealed. This embodiment has the structure and functions similar to the embodiment in FIG. 1 and FIG. 2. The difference between this embodiment and the above one is in that the carrier layer 30 in the above embodiment is attached and connected to the eye part 11 of the colloidal layer 20 horizontally and perpendicular to the central line Z of the facial mask 10 (user's face) while the carrier layer 30 in this embodiment is attached and connected to the eye part 11 of the colloidal layer 20 horizontally and extended over the area above the eye part 11, as shown in FIG. 3 and FIG. 4. The carrier layer 30 covers over the upper half part of the colloidal layer 20.

Figure 6:
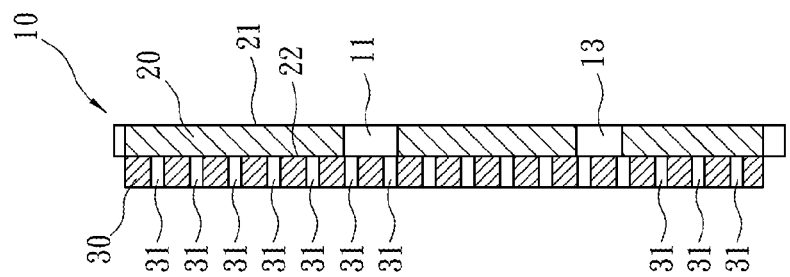
FIG. 6 is a schematic drawing showing an enlarged lateral cross section view of the embodiment in FIG. 5 according to the present invention.
Figure 5:
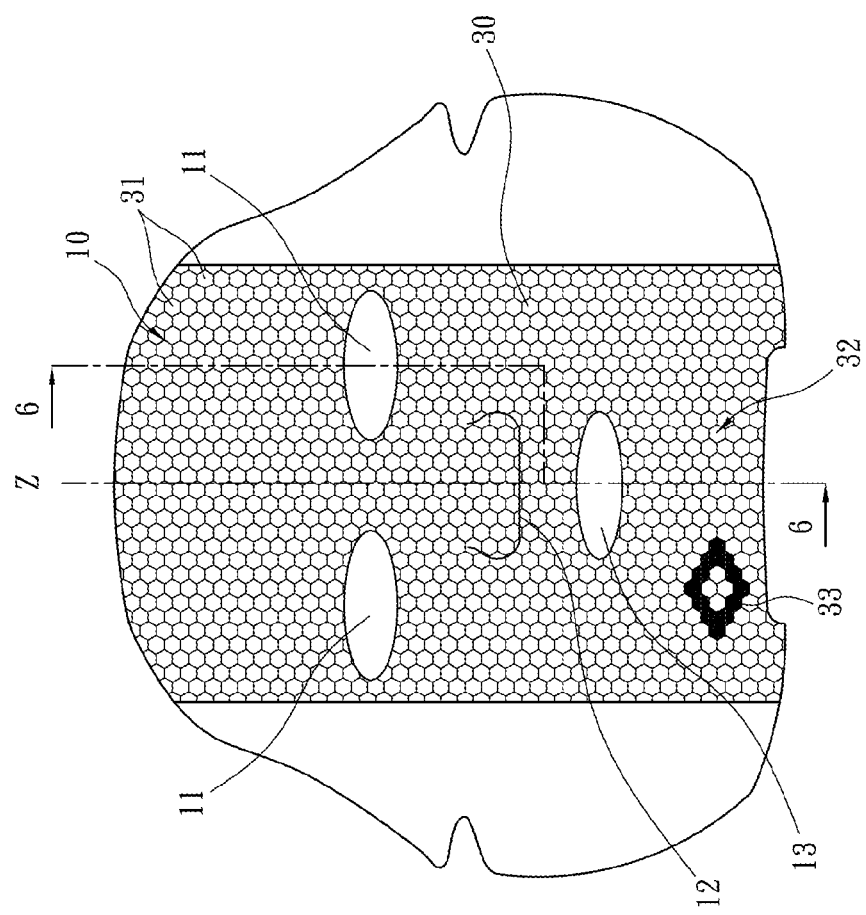
FIG. 5 is a schematic drawing showing a front view of a further embodiment of the present invention.

Refer to FIG. 5 and FIG. 6, a further embodiment is revealed. This embodiment has the structure and functions similar to the embodiment in FIG. 1 and FIG. 2. The difference between this embodiment and the above one is in that the carrier layer 30 in the above embodiment is attached and connected to the eye part 11 of the colloidal layer 20 horizontally while the carrier layer 30 in this embodiment is vertically attached and connected to the central part of the colloidal layer 20, along the central line Z of the facial mask 10. The central part is defined as the area bilaterally symmetrical along the central line of the facial mask, extended from forehead downward to the lower jaw of the facial mask 10 and including the eye part 11, the nose part 12, and the mouth part 13.

Figure 7:
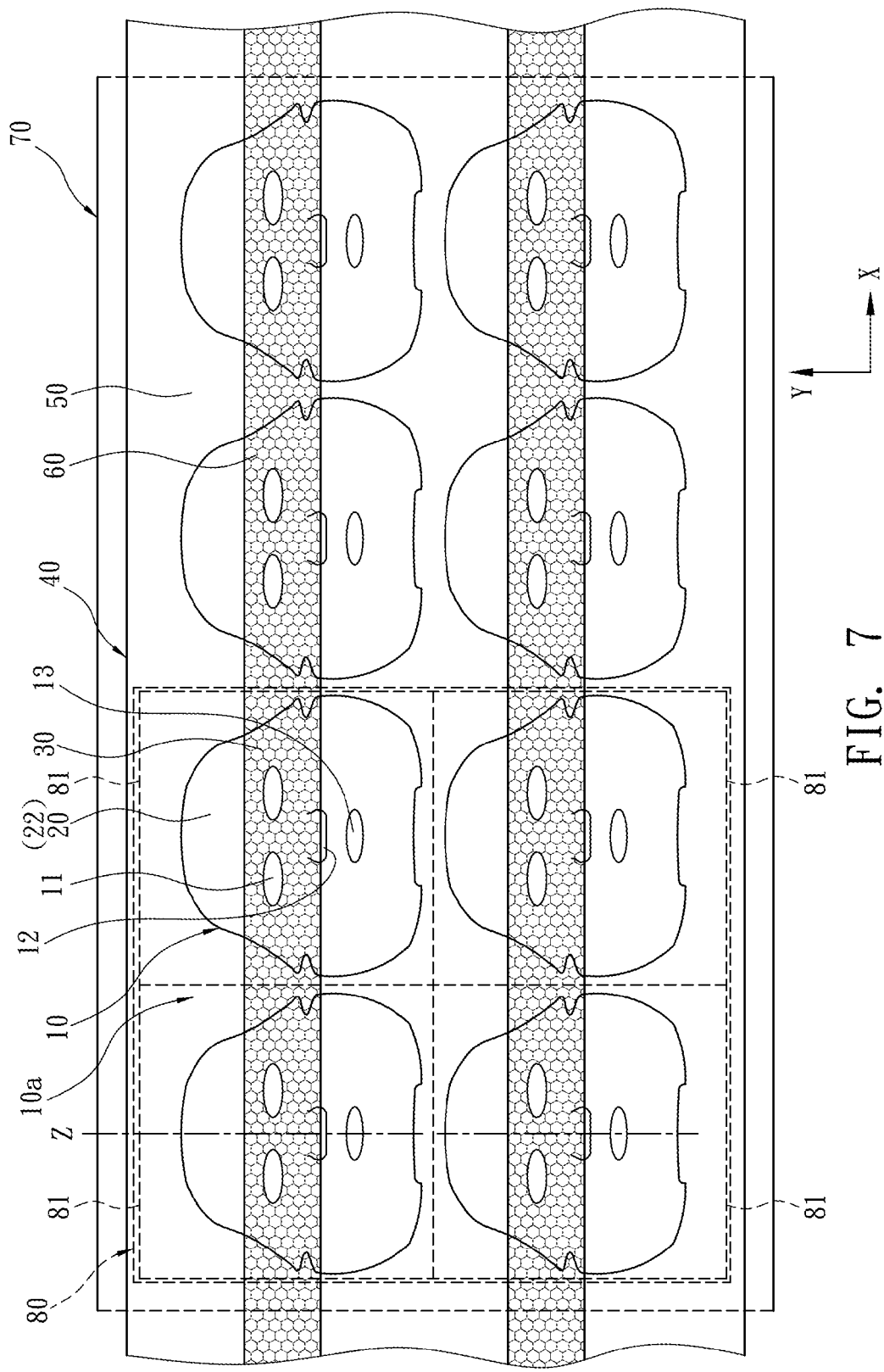
FIG. 7 is a schematic drawing showing a top view during manufacturing processes of the embodiment in FIG. 1 according to the present invention.
Figure 8:
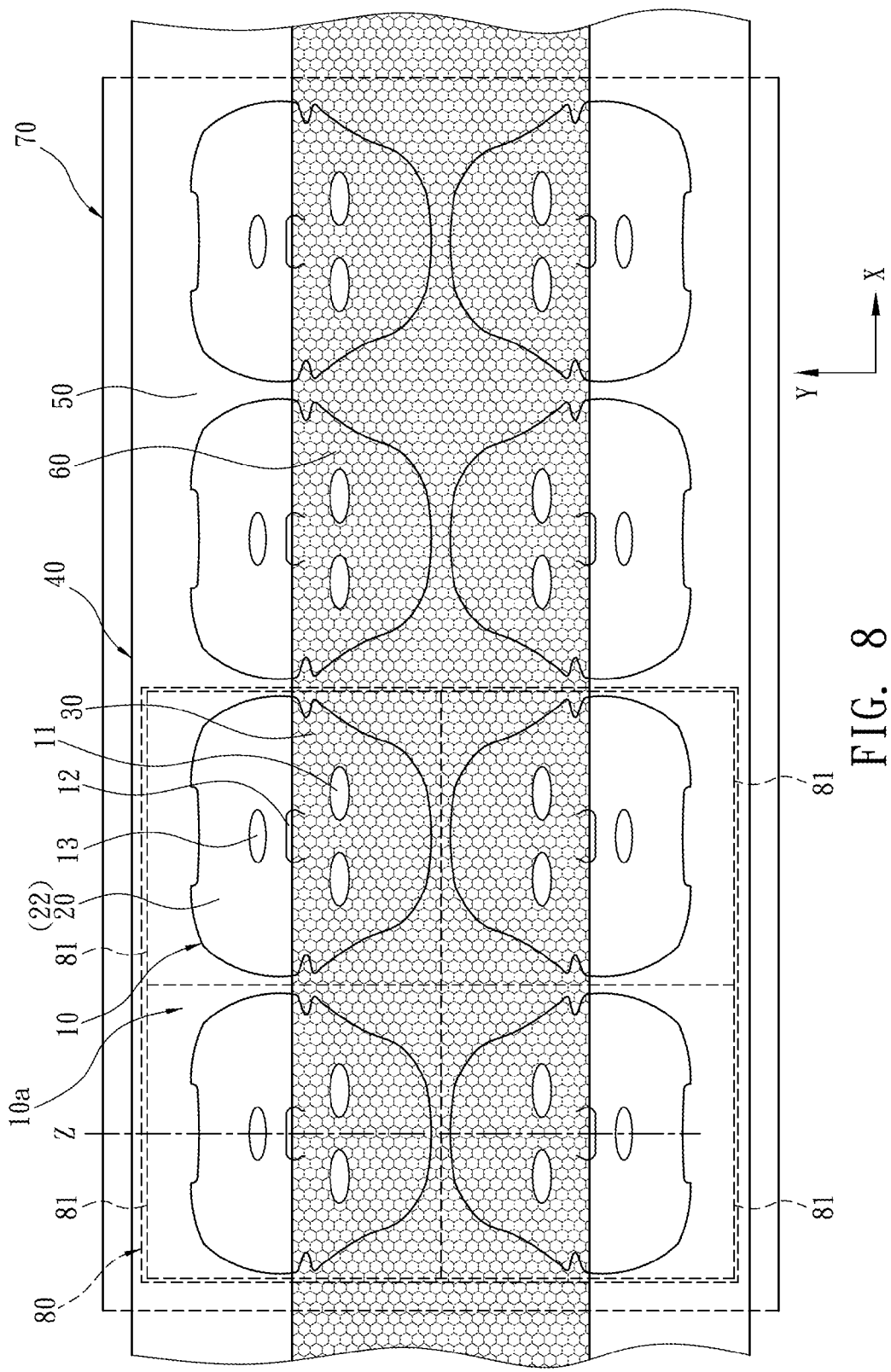
FIG. 8 is a schematic drawing showing a top view during manufacturing processes of the embodiment in FIG. 3 according to the present invention.
Figure 9:
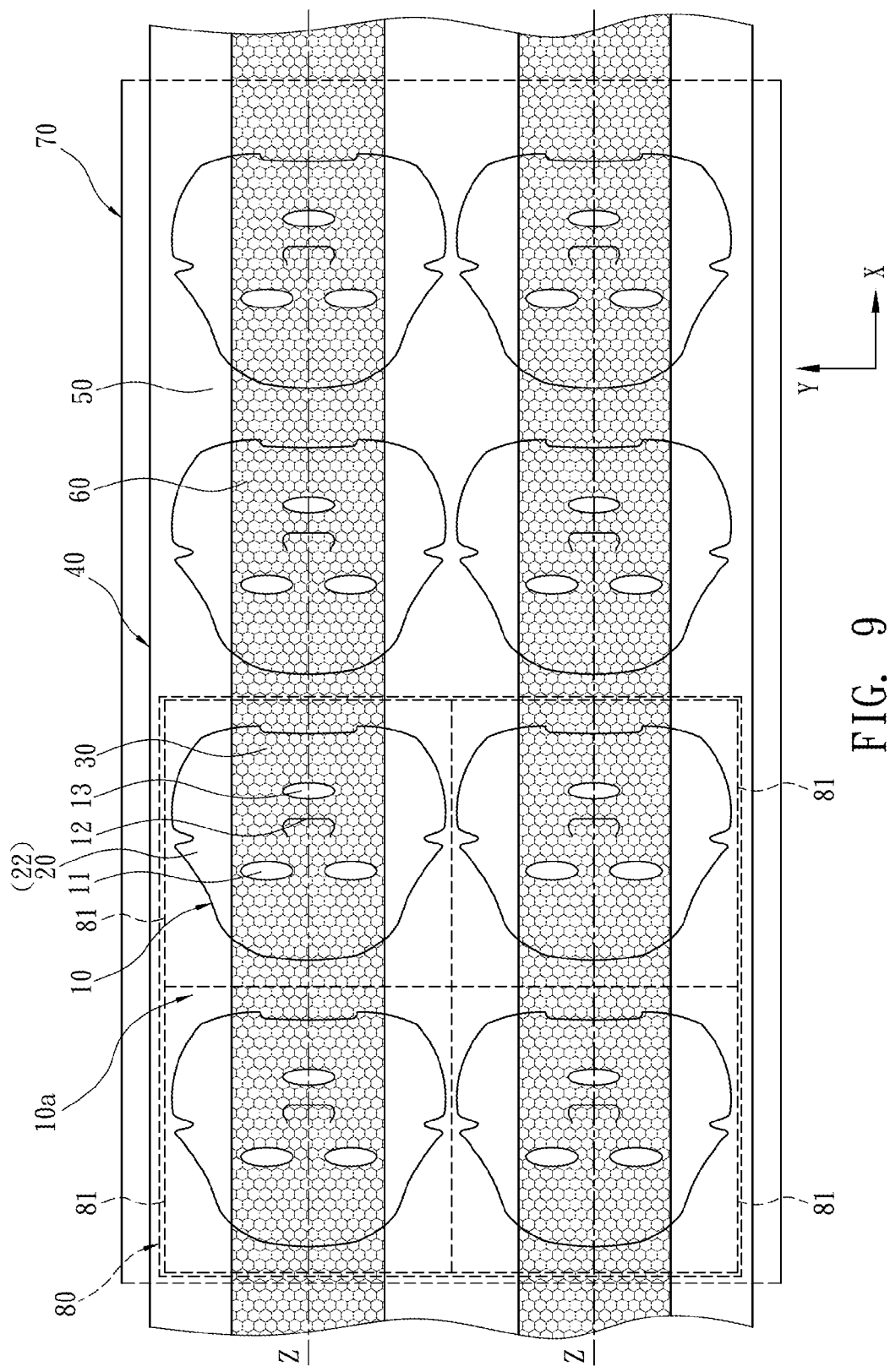
FIG. 9 is a schematic drawing showing a top view during manufacturing processes of the embodiment in FIG. 5 according to the present invention.

Refer to FIG. 7, FIG. 8 and FIG. 9, a method for manufacturing a colloidal facial mask 10 of the present invention includes following steps. Step 1: provide a continuous base material for colloidal facial masks 40 on a conveying platform 70 for cutting. The base material for colloidal facial masks 40 is moved along a conveying direction X (the arrow X indicates in FIG. 7 to FIG. 9) of the conveying platform 70. The continuous base material for colloidal facial masks 40 includes a continuous colloidal layer 50 and at least one continuous carrier layer 60. The continuous colloidal layer 50 consists of a first surface 21 and a second surface 22 opposite to the first surface 21 (refer to FIG. 2, FIG. 4 and FIG. 6). The continuous carrier layer 60 is horizontally attached to, connected to and covered at least a partial area of the second surface 22 of the continuous colloidal layer 50 along the conveying direction X of the conveying platform 70. As shown in FIG. 7 and FIG. 9, there are two continuous carrier layers 60 horizontally attached and connected to the second surface 22 of the continuous colloidal layer 50 along the conveying direction X and occupied two partial areas at different positions of the second surface 22. Refer to FIG. 8, there is one continuous carrier layer 60 horizontally attached and connected to the second surface 22 of the continuous colloidal layer 50 along the conveying direction X and occupied one partial area on the second surface 22. Moreover, respective continuous carrier layer 60 can be arranged at different positions on the second surface 22 of the continuous colloidal layer 50 according to requirements in use or during manufacturing. For example, the arrangement of the continuous carrier layer 60 in FIG. 8 is different from those in FIG. 7, FIG. 8 and FIG. 9.

Step 2: use a cutting tool 80 disposed with at least one cutting die for facial masks 81 thereof to cut the continuous base material for colloidal facial masks 40 on the conveying platform 70 for formation of colloidal masks 10. Thereby a facial mask array 10a including at least one facial mask 10 arranged at a specific pattern (including the direction or the number) is obtained. The facial mask array 10a formed by a plurality of the colloidal masks 10 is preferred for increasing the speed of the cutting operation. Moreover, the angle of the cutting die for facial masks 81 on the cutting tool 80 is adjustable according to requirements of the cutting operation. The details are described in the following. Take the facial mask array 10a as an example. During the cutting operation, the previous facial mask array 10a being cut and formed is moved along the conveying direction X of the conveying platform 70 continuously and then the next facial mask array 10a is cut and formed by the cutting tool 80 cutting the base material for colloidal facial masks 40 again. In each colloidal mask 10 of the facial mask array 10a, the carrier layer 30 is located on at least one partial area of the second surface 22 of the colloidal layer 20 corresponding to the eye part 11, the nose part 12, and the mouth part 13 of the facial mask 10, or two of their combinations. As to the number and arrangement of the facial mask 10 of the facial mask array 10a, there is no restriction on them. The number and the arrangement vary according to the requirements of the cutting tool 80 (refer to FIG. 10), the conveying platform 70, or the colloidal masks 10. Refer to FIG. 7, FIG. 8 and FIG. 9, there are eight colloidal masks 10 cut and formed on the conveying platform 70. The colloidal masks 10 are arranged at four columns along the conveying direction X and there are two colloidal masks 10 disposed in the direction Y that is perpendicular to the direction X (two rows). Each column has two colloidal masks 10 and there are four columns (2×4=8). The facial mask array 10a can also be a 2 by 1 array (2×1=2), a 2 by 2 array (2×2=4), a 2 by 3 array (2×3=6), or a 2 by 4 array (2×4=8). Users can choose suitable arrangement according to requirements for manufacturing processes. Refer to FIG. 7, a top view of another embodiment shown in FIG. 1 and FIG. 2 during manufacturing is revealed. The central line Z of each facial mask 10 in each column is arranged at the same direction. Refer to FIG. 8, a top view of another embodiment shown in FIG. 3 and FIG. 4 during manufacturing is revealed. The central lines Z of the two facial masks 10 in each column are disposed on the opposite directions. Refer to FIG. 9, a top view of a further embodiment shown in FIG. 5 and FIG. 6 during manufacturing is revealed. The central lines Z of the two facial masks 10 in each column are arranged in parallel.

Step 3: take out each colloidal facial mask 10 to complete continuous manufacturing processes of the colloidal facial mask 10. Then the following processes such as packaging are performed.

Figure 10:
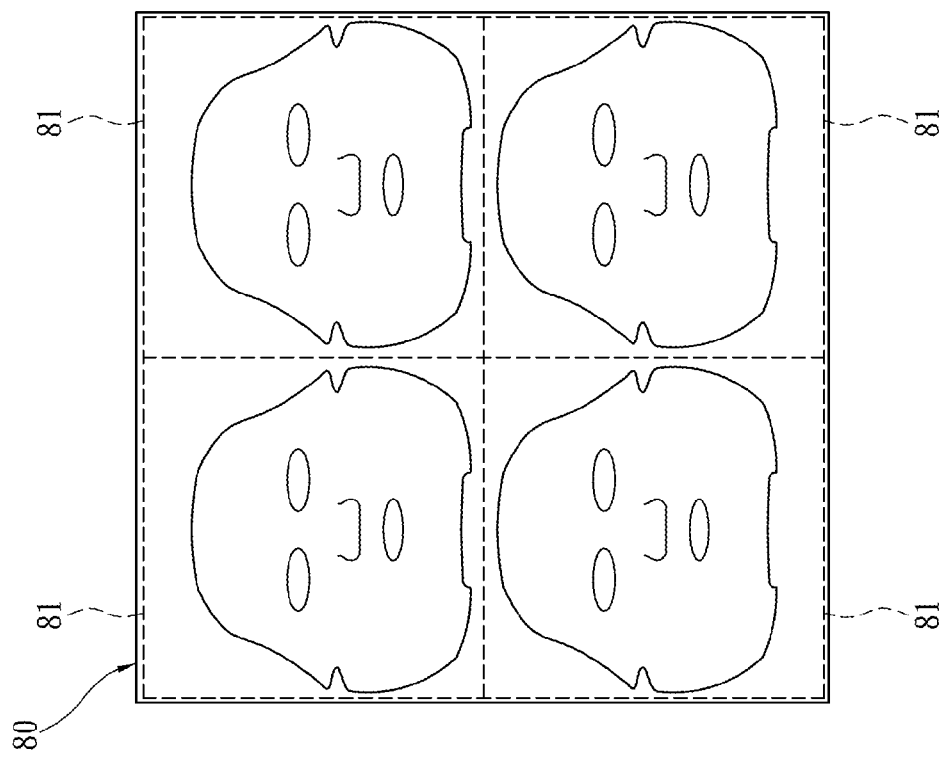
FIG. 10 is a schematic drawing showing a top view of a cutting tool (cutting die for facial mask) used during the manufacturing processes shown in FIG. 7 according to the present invention.
Figure 11:
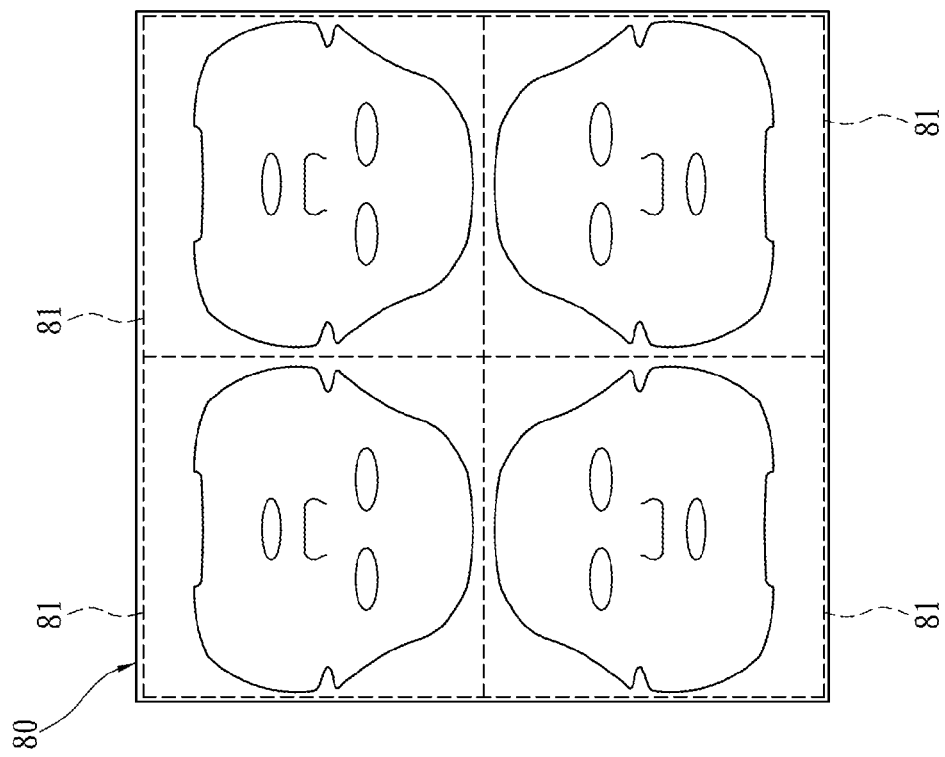
FIG. 11 is a schematic drawing showing a top view of a cutting tool (cutting die for facial mask) used during the manufacturing processes shown in FIG. 8 according to the present invention.
Figure 12:
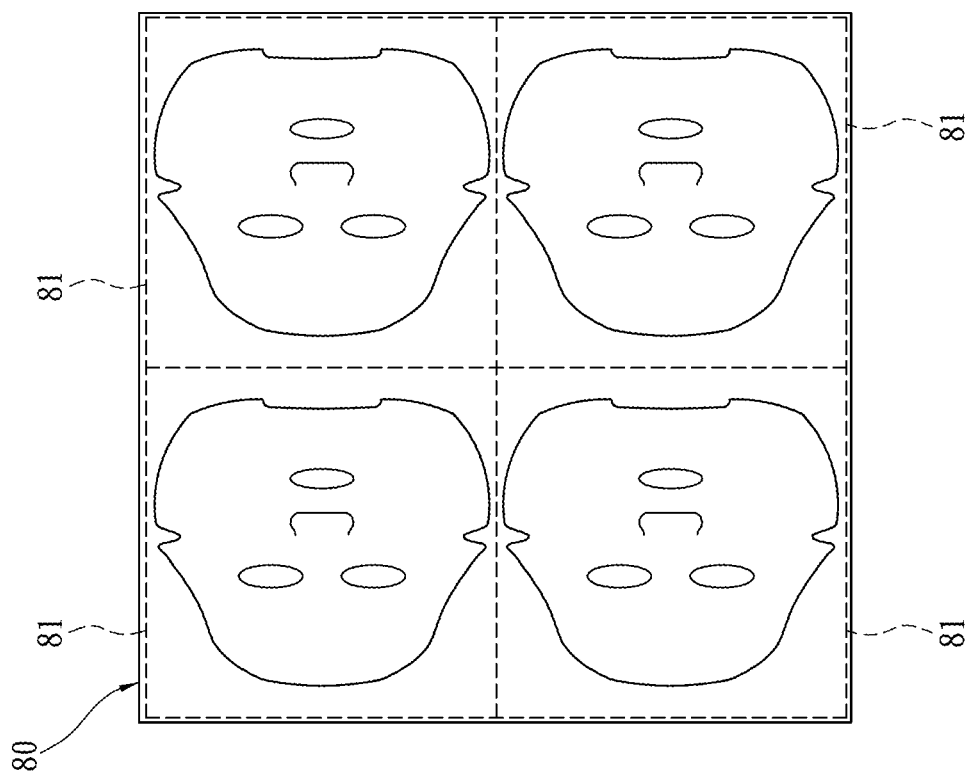
FIG. 12 is a schematic drawing showing a top view of a cutting tool (cutting die for facial mask) used during the manufacturing processes shown in FIG. 9 according to the present invention.

In addition, in the step 2, the cutting tool 80 is disposed with at least one cutting die for facial mask 81. The arrangement of the colloidal facial masks 10 in the facial mask array 10a is not restricted. Refer to FIG. 7, FIG. 8 and FIG. 9, the shape of each colloidal facial mask 10 in the facial mask array 10a of the embodiments is the same but the arrangement of the colloidal facial masks 10 in the facial mask array 10a of the embodiment is different from one another. The cutting tool 80 used for cutting a facial mask array 10a can be disposed with a plurality of cutting dies 81 each of which used for cutting a facial mask. As shown from FIG. 7 to FIG. 12, the cutting tool 80 can be, but not limited to, disposed with four cutting dies 81. The direction or arrangement way of the cutting dies for facial masks 81 can be different. As shown in FIG. 7 to FIG. 9, the direction or arrangement way of the cutting dies for facial masks 81 is adjusted for changing directions or arrangement of each colloidal facial mask 10 in the facial mask array 10a. Take the cutting tool 80 disposed with four cutting dies for facial masks 81 as an example. During manufacturing processes shown in FIG. 7, the four cutting dies for facial masks 81 of the cutting tool 80 are arranged in the same directions, as shown in FIG. 7 and FIG. 10. Once the manufacturing processes are changed to the manufacturing processes shown in FIG. 8, two of the four cutting dies for facial masks 81 are rotated 180 degrees respectively to be opposite to the other two cutting dies for facial masks 81, as shown in FIG. 8 and FIG. 11. If the manufacturing processes are switched to the manufacturing processes shown in FIG. 9, each of the four cutting dies for facial masks 81 are rotated 90 degrees respectively, as shown in FIG. 9 and FIG. 12. In order to make the colloidal facial masks 10 being cut have the same shape, or make the colloidal facial masks 10 in the facial mask array 10a have different directions or arrangement as shown in FIG. 7, FIG. 8 and FIG. 9, the direction and position of each cutting dies for facial masks 81 in the cutting tool 80 can be adjusted. Thus the production cost of the cutting dies for facial masks 81 and the cutting tool 80 can be saved. This is beneficial to mass production.

Figure 13:
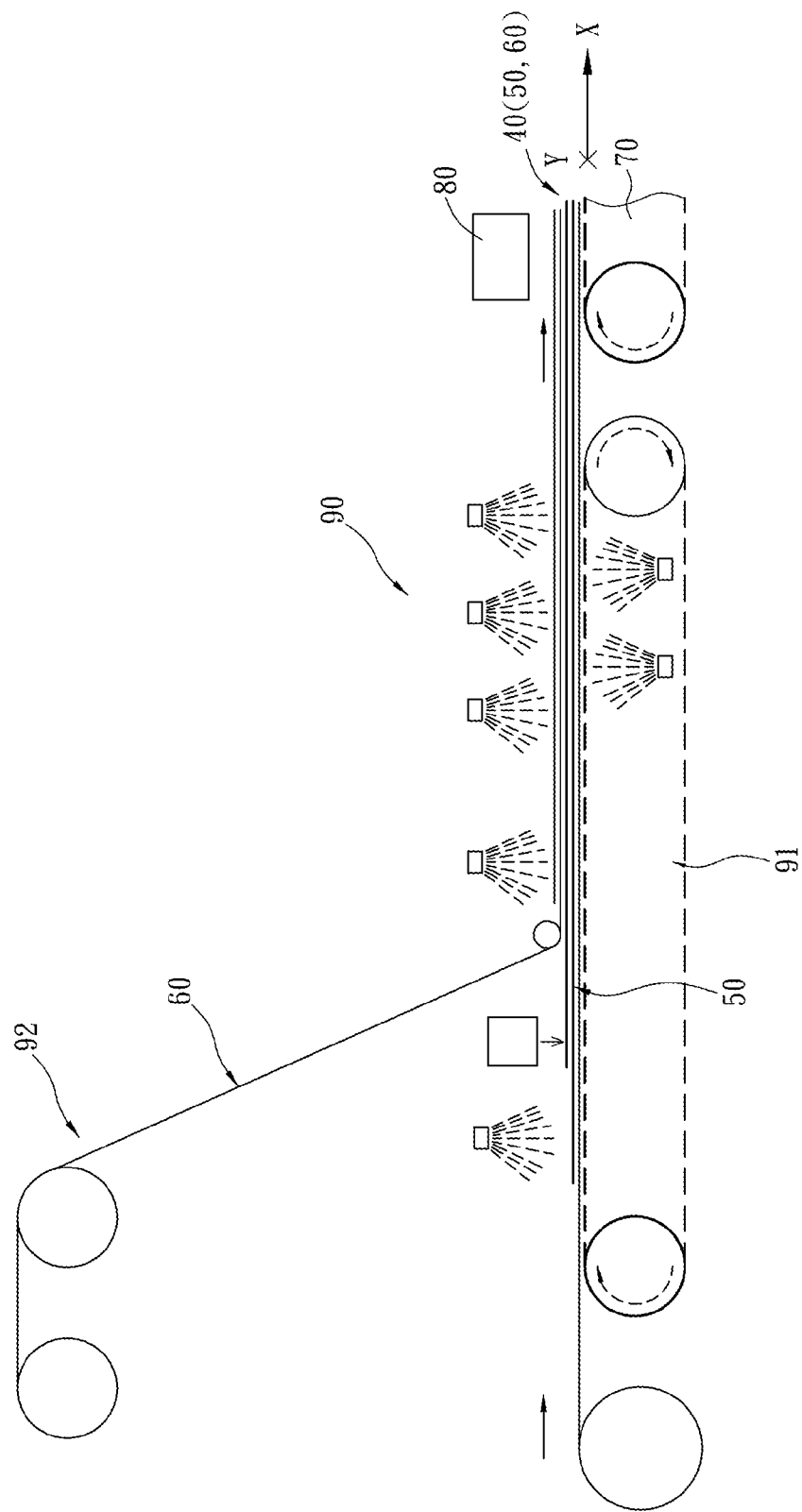
FIG. 13 is a schematic drawing showing an embodiment of an apparatus for continuously manufacturing films of an embodiment according to the present invention.

Refer to FIG. 13, the conveying platform 70 for cutting operation is a circulating conveying platform moving along the conveying direction X, connected to and located after an apparatus for continuously manufacturing films 90 (an output end along the conveying direction X). Thus the continuous base material for colloidal facial masks 40 (having the continuous colloidal layer 50 and the continuous carrier layer 60) is transported to the conveying platform 70 and moved along the conveying direction X. Then the continuous base material for colloidal facial masks 40 is cut by the cutting tool 80 during the movement along the conveying direction X. As to mechanical design of the apparatus for continuously manufacturing films 90, it includes a circulating conveying platform 91 and a carrier layer providing device 92. The manufacturing of the continuous colloidal layer 50 is finished at the circulating conveying platform 91. Then the continuous carrier layer 60 is attached and connected to the continuous colloidal layer 50 at the carrier layer providing device 92.

After being produced, the colloidal facial mask 10 with a partial carrier of the present invention is a moisture film that is soaked and received in a closed bag such as aluminum foil bag or bubble bag. The colloidal layer of the colloidal facial mask 10 contains 95% water. The closed bag can be filled with solutions for cosmetic use but not limited. The colloidal facial mask 10 with a partial carrier can further be dried to form a dry film. There are various ways of drying including freeze-drying, air drying, heat drying, far-infrared drying, microwave drying, etc. The water contained in the colloidal layer of the colloidal facial mask 10 is no more than 20% after being tried. A plurality of dry films can be stacked and stored in a moisture barrier bag. While in use, the dry film can be turned back to the moisture state by being soaked or other ways.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A colloidal facial mask with a partial carrier comprising a colloidal layer and a carrier layer; wherein the colloidal facial mask is mounted with through holes corresponding to an eye part, a nose part, and a mouth part so that the eye part, the nose part, and the mouth part are exposed;
   wherein the colloidal layer is made from colloidal film materials with high water absorption for absorbing solutions and has a first surface and a second surface opposite to the first surface; wherein the first surface is attached to a user's face so that the solutions are in contact with skin of the user's face; and
   wherein the carrier layer is attached and connected to at least one partial area of the second surface of the colloidal layer; the partial area includes the area around the through holes corresponding to the eye part, the nose part, the mouth part or their combinations; and at least one area of the second surface of the colloidal layer is not covered by the carrier layer.

2. The colloidal facial mask as claimed in claim 1, wherein a material for the colloidal layer is selected from the group consisting of alginate, polymer gel, and bio-cellulose.

3. The colloidal facial mask as claimed in claim 1, wherein the carrier layer is made from knitted fabric including lace fabric, woven fabric, and Jacquard fabric.

4. The colloidal facial mask as claimed in claim 3, wherein the carrier layer made from the knitted fabric is further disposed with at least one knitted pattern and the knitted pattern includes uniform pattern, non-uniform pattern or their combinations.

5. The colloidal facial mask as claimed in claim 4, wherein the knitted pattern is further disposed with at least one marker and the marker includes a brand log, a design pattern, a hollow-out pattern or their combinations.

6. The colloidal facial mask as claimed in claim 1, wherein the carrier layer is made from non-woven fabric.

7. The colloidal facial mask as claimed in claim 6, wherein a plurality of insertion holes is arranged at the carrier layer made from the non-woven fabric.

8. The colloidal facial mask as claimed in claim 6, wherein at least one hollow-out pattern is disposed on the carrier layer made from the non-woven fabric.

9. The colloidal facial mask as claimed in claim 6, wherein at least one marker is arranged at the carrier layer made from the non-woven fabric and the marker includes a brand logo, a design pattern, a hollow-out pattern or their combinations.

10. The colloidal facial mask as claimed in claim 1, wherein the carrier layer is horizontally attached and connected to the area around the through holes corresponding to the eye part of the colloidal layer, perpendicular to a central line of the colloidal facial mask.

11. The colloidal facial mask as claimed in claim 1, wherein the carrier layer is attached and connected to the area around the through holes corresponding to the eye part of the colloidal layer horizontally, perpendicular to a central line of the colloidal facial mask and extended over area above the eye part; the carrier layer is covered over an upper half part of the colloidal layer.

12. The colloidal facial mask as claimed in claim 1, wherein the carrier layer is vertically attached and connected to a central part of the colloidal layer, along the central line of the facial mask; thus the carrier layer is bilaterally symmetrical along the central line of the facial mask, extended from forehead downward to lower jaw of the facial mask and including the area around the through holes corresponding to the eye part, the nose part, and the mouth part.

13. A method for manufacturing a colloidal facial mask with a partial carrier, wherein the colloidal facial mask is mounted with through holes corresponding to an eye part, a nose part, and a mouth part so that the eye part, the nose part, and the mouth part are exposed, comprising the steps of:
   Step 1: providing a continuous base material for the colloidal facial mask on a conveying platform for cutting; the base material for colloidal facial masks is moved along a conveying direction of the conveying platform; the continuous base material for the colloidal facial mask includes a continuous colloidal layer and at least one continuous carrier layer; wherein the continuous colloidal layer includes a first surface and a second surface opposite to the first surface; the continuous carrier layer is horizontally attached to, connected to the second surface of the continuous colloidal layer along the conveying direction of the conveying platform and covered at least a partial area of the second surface of the continuous colloidal layer, wherein the partial area includes the area around the through holes corresponding to the eye part, the nose part, the mouth part or their combinations;
   Step 2: using a cutting tool disposed with at least one cutting die for facial masks to cut the continuous base material for colloidal facial masks and get a facial mask array including at least one facial mask; wherein the previous facial mask array being cut and formed is moved along the conveying direction of the conveying platform continuously and then the next facial mask array is cut and formed by the cutting tool cutting the base material for colloidal facial masks again; wherein the carrier layer on the colloidal mask of the facial mask array is located on at least one partial area of the second surface of the colloidal layer and the partial area of the second surface of the colloidal layer includes the area around the through holes corresponding to the eye part, the nose part, the mouth part or their combinations;

Step 3: taking out the colloidal facial mask of the facial mask array to complete continuous manufacturing processes of the colloidal facial mask.

14. The method as claimed in claim 13, wherein directions and positions of the cutting die for facial masks disposed on the cutting tool are adjustable according to directions and positions of the colloidal mask of the facial mask array.

15. The method as claimed in claim 14, wherein the cutting die for facial masks disposed on the cutting tool is able to be rotated an angle in relative to the conveying direction of the conveying platform and the angle is selected from the group consisting of 90 degrees and 180 degrees.

* * * * *